United States Patent [19]

Turbak et al.

[11] Patent Number: 4,500,546
[45] Date of Patent: Feb. 19, 1985

[54] SUSPENSIONS CONTAINING MICROFIBRILLATED CELLULOSE

[75] Inventors: Albin F. Turbak, Convent Station; Fred W. Snyder, Wharton, both of N.J.; Karen R. Sandberg, Shelton, Wash.

[73] Assignee: International Telephone and Telegraph Corporation, New York, N.Y.

[21] Appl. No.: 441,686

[22] Filed: Nov. 15, 1982

Related U.S. Application Data

[62] Division of Ser. No. 202,740, Oct. 31, 1980, Pat. No. 4,378,381.

[51] Int. Cl.³ .............................................. A61K 47/00
[52] U.S. Cl. .................................................... 514/781
[58] Field of Search ......................................... 424/362

[56] References Cited

U.S. PATENT DOCUMENTS

| | | | |
|---|---|---|---|
| 3,920,821 | 11/1975 | Schröder et al. | 424/263 |
| 4,183,898 | 1/1980 | Liff | 424/63 |
| 4,246,285 | 1/1981 | Van Duzee | 424/358 |

FOREIGN PATENT DOCUMENTS

1300820 12/1972 United Kingdom.

Primary Examiner—Sidney Marantz
Assistant Examiner—Shawn P. Foley
Attorney, Agent, or Firm—James B. Raden; Harold J. Holt

[57] ABSTRACT

A suspension of a finely divided material in a liquid suspending medium which swells cellulose, the suspension containing microfibrillated cellulose in an amount sufficient to produce a stable, homogeneous suspension. The microfibrillated cellulose, a form of cellulose having a very large available surface area per unit of weight, acts to confer, among other benefits, greater stability on the suspension. The suspensions are useful in a variety of end use products including foods, cosmetics, pharmaceuticals, paints and drilling muds.

4 Claims, No Drawings

SUSPENSIONS CONTAINING MICROFIBRILLATED CELLULOSE

This application is a divisional application of Ser. No. 202,740 filed Oct. 31, 1980, U.S. Pat. No. 4,378,381.

This invention relates to stable homogeneous suspensions containing microfibrillated cellulose.

In our copending application, Ser. No. 107,446, filed Dec. 26, 1979, now abandoned, refiled as continuation application, Ser. No. 313,726, U.S. Pat. No. 4,374,702, there is disclosed a new type of cellulose, denominated microfibrillated cellulose, distinguished from prior celluloses by a vastly increased surface area, greater liquid absorption characteristics and greater reactivity. The microfibrillated cellulose there disclosed is prepared by repeatedly passing a liquid suspension of fibrous cellulose through a high pressure homogenizer until the cellulose suspension becomes substantially stable. The process converts the cellulose into microfibrillated cellulose without substantial chemical change.

It has been discovered that the aforementioned microfibrillated cellulose has the unique capability of enhancing the homogeneity and stability of a wide variety of suspensions. The presence of microfibrillated cellulose in suspensions of the type used in foods, cosmetics, pharmaceuticals and such industrial products as paints and drilling muds has been found to confer a number of unusual property characteristics on the resulting product. In some cases, suspensions may be made which were not previously possible. The microfibrillated cellulose may be formed in situ in the suspension in a single stage operation by mixing fibrous cellulose with the ingredients of the suspension and then passing the mixture through an homogenizer or alternatively, the microfibrillated cellulose may be separately prepared and added to the suspension after preparation.

Specifically, the invention involves a suspension of finely divided material in a liquid suspending medium which swells cellulose, the suspension containing microfibrillated cellulose in an amount sufficient to produce a stable, homogeneous suspension. The suspension is prepared in situ by mixing together a liquid which swells cellulose, a finely divided material suspended in said liquid and fibrous cellulose to form a liquid suspension and repeatedly passing the liquid suspension through a small diameter orifice in which the mixture is subjected to a pressure drop of at least 3000 psi and a high velocity shearing action followed by a high velocity decelerating impact, the process of converting the cellulose into microfibrillated cellulose, the microfibrillated cellulose being present in an amount sufficient to form a stable homogeneous suspension of the liquid and suspended material. Alternatively, the suspension may be prepared by mixing together the liquid which swells cellulose, the finely divided material suspended in the liquid and the separately prepared microfibrillated cellulose in an amount sufficient to form a stable, homogeneous suspension of the liquid and suspended material.

There is an obvious cost savings in preparing the microfibrillated cellulose and the suspension in a single stage operation. In addition, there is also in certain instances a product advantage which results in the use of the single stage technique. The use of this single stage technique in the preparation of certain food products is the subject of parent applicaton Ser. No. 202,740, filed of even date herewith now U.S. Pat. No. 4,378,381. In certain products, the heat build-up that accompanies the fibrillation process is detrimental and for such heat sensitive systems the separate preparation of microfibrillated cellulose is necessary.

The term suspension as used herein is intended to include within its scope, suspensions in which a finely divided solid, liquid or gas are mixed with, but undissolved in, a liquid. The term thus includes an emulsion in which a liquid is dispersed in a second immiscible liquid, and a foam in which a gas is entrapped in the liquid and stabilized.

The amount of microfibrillated cellulose used in preparing the suspensions of the invention will vary considerably depending on the nature and intended use of the suspension. For example, it has been found that oil-in-water emulsions may be rendered stable with 1% by weight or less of microfibrillated cellulose. The properties of latex paint suspensions are enhanced with as little as 0.25% of microfibrillated cellulose while sand suspensions are stabilized with from 2 to 3% of microfibrillated cellulose. At the other extreme, the microfibrillated cellulose may be present as the predominant or major ingredient of the suspension. In general, the microfibrillated cellulose should be present in an amount sufficient to accomplish its function of producing a stable, homogeneous suspension. In most applications, this amount will range from about 0.25% to about 5%, the percentages being the weight of cellulose solids present as microfibrillated cellulose based on the total weight of the suspension.

The preparation of the microfibrillated cellulose, either in situ in the suspension or separately, is assisted by the addition to the starting mixture of a hydrophilic polymer which may be a cellulose ester or ether, a synthetic acid polymer (or copolymer), a natural gum or a starch. Examples of such hydrophilic polymers are carboxymethyl cellulose, methyl cellulose (methocel), hydroxypropyl cellulose, polyacrylic acid, carageenin and guar gum. Addition of the hydrophilic polymer to the liquid suspending medium, prior to cellulosic pulp addition, appears to prevent dewatering of the pulp (or other fibrous cellulose) under the high pressures of the fibrillation process and thus allows the slurry to pass through the homogenizer at higher slurry concentrations. Moreover, the microfibrillated cellulose produced with the additive present also displays improved freeze-thaw stability and improved dewatering resistance under pressure and thus produces improved suspensions in accordance with the invention in those products where smoothness is important, as for example in hand creams, cosmetics and paints. The hydrophilic polymer will enhance the fibrillation process at levels as low as 0.1% by weight of the suspension, and may be used in amounts as high as 25%, depending on the nature of the suspension.

The following examples illustrate the practice of the invention. Unless otherwise indicated, all parts and percentages are by weight.

EXAMPLE 1

A 4% cellulose slurry in approximately 3 gallons of water was prepared using prehydrolyzed kraft pulp which had been cut to pass through a 0.125 inch screen. The starting temperature of the slurry was 25° C. The slurry was passed through a Manton-Gaulin (trademark) homogenizer at 8000 lbs/sq. in. (gauge) ten consecutive times until a stable suspension or gel-point was reached.

Microfibrillated cellulose can be used to adjust the rheology of paint to reduce dripping. In addition, the microfibrillated cellulose assists in the coverage of the surface to be painted and thus reduces the required levels of titanium dioxide pigment. This is illustrated by Examples 2-7.

EXAMPLES 2-7

The microfibrillated cellulose of Example 1 was added as a 4% slurry in water to a commerical latex enamel white paint. A comparison of the drip length of the paint at various solid levels with and without various percentages of microfibrillated cellulose addition is set forth in Table I.

TABLE I

| Example | % MFC | % Pigment | % Solids | % Vehicle | Drip Length (Inches) |
|---|---|---|---|---|---|
| 2 | 0 | 15.97 | 15.97 | 84.03 | 8.8 |
| 3 | 0.25 | 15.72 | 15.97 | 84.03 | 8.2 |
| 4 | 0 | 15.34 | 15.34 | 84.66 | 8.5 |
| 5 | 0.50 | 14.84 | 15.34 | 84.66 | 6.0 |
| 6 | 0 | 14.06 | 14.06 | 85.93 | 12.0 |
| 7 | 1.0 | 13.06 | 14.06 | 85.93 | 4.0 |

It will be apparent from Table I that an amount of microfibrillated cellulose as low as 0.25% reduces dripping of the paint and that at a level of 1%, dripping as measured by drip length is one third of that of an equivalent solids percent paint without microfibrillated cellulose.

Microfibrillated cellulose acts as a non-ionic emulsifying agent as well as a stabilizer for emulsions. This is illustrated by the following examples.

EXAMPLES 8-16

A 4.7% solids microfibrillated cellulose slurry in water was prepared as in Example 1 from sulfite pulp. The slurry was then intimately mixed with food grade soybean oil and additional water in a blender. Table II sets forth the results of a series of experiments with and without microfibrillated cellulose and with various quantities of microfibrillated cellulose, oil and added water to prepare an oil-in-water emulsion.

TABLE II

| Example | MFC Slurry Grams | Oil Grams | Water Added Grams | % MFC | % Oil | Result |
|---|---|---|---|---|---|---|
| 8 | 0 | 40 | 160 | 0 | 20 | Stable emulsion not possible |
| 9 | 10.6 | 40 | 150 | 0.25 | 20 | Stable emulsion not possible |
| 10 | 25 | 44 | 150 | 0.54 | 20 | Stable emulsion not possible |
| 11 | 40 | 40 | 120 | 0.94 | 20 | Stable emulsion |
| 12 | 40 | 80 | 80 | 0.94 | 40 | Stable emulsion |
| 13 | 70 | 251 | 30 | 0.94 | 71.5 | Stable emulsion |
| 14 | 50 | 64 | 51 | 1.42 | 38.8 | Stable emulsion |
| 15 | 85 | 176 | 15 | 1.45 | 63.8 | Stable emulsion |
| 16 | 85 | 100 | 15 | 2.0 | 50 | Stable emulsion |

It is apparent from the data in Table II that small amounts of microfibrillated cellulose are able to stabilize emulsions containing up to 71.5% oil.

EXAMPLE 17

To demonstrate that stable emulsions can be made in situ (i.e. without separate preparation of the microfibrillated cellulose), a 20% by weight stable emulsion was prepared from 80 grams of pulp which had been cut to pass through a 0.125 inch screen, 800 grams of a liquid vegetable oil (a food grade oil sold under the trademark Crisco) and 3112 grams of water. The entire mixture was passed through an homogenizer at 8000 psig for ten passes. The final emulsion contained about 2% microfibrillated cellulose and was stable on the shelf at room temperature for at least six months.

Microfibrillated cellulose is also capable of use in relatively small, economical proportions for the preparation of stable emulsions of dense solids such as sand and coal for pipeline coal slurry pumping. The following examples demonstrate the usefulness of microfibrillated cellulose for use as "packer fluids" of the type used for preventing settling of suspended material during shutdown of drilling operations.

EXAMPLE 18

A 2% suspension in water of cellulosic pulp cut to pass through a 0.125 inch screen was prepared as a control. To 100 grams of this suspension was added about 10 grams of ordinary sand. The mixture was shaken and allowed to stand. As expected, the sand settled rapidly to the bottom—no suspending action was noted.

EXAMPLE 19

To a sample of 100 grams of a 2% slurry of microfibrillated cellulose in water, about 10 grams of sand was added and the mixture was shaken. Upon standing, the sand remained suspended for over three months. Unlike most polymeric thickened suspensions, the suspension was stable even if heated to 100° C.

A second experiment was performed in which a layer of the sand was placed on top of a layer of the microfibrillated cellulose. Again, the sand did not settle through the microfibrillated cellulose and did not penetrate it appreciably over a period of months.

Microfibrillated cellulose thus may be used at low concentrations (2 to 3%) and therefore inexpensively in drilling operations and for enhancing the stability of suspensions of relatively dense solids.

There is currently an active interest in the food industry in the use of gums, or other substitute for oil, to produce "no-oil" salad dressings. It has been found that microfibrillated cellulose may be substituted for oil to produce a low calorie salad dressing. The product obtained from mixing a commerical Italian dressing mix yields a stable suspension of spices which are uniformly distributed throughout the mix. A commercial Thousand Island mix with microfibrillated cellulose yields a creamy stable suspension similar to the texture of its oil base counterpart. Commercial preparations of Italian salad dressings generally require shaking before use. The corresponding product made with microfibrillated cellulose does not.

EXAMPLE 20

A vinegar solution was approximated by preparing a 5% (V/V) acetic acid solution. Fifty-five milliliters of this vinegar was added to 25 ml of water in a cruet. In place of oil, 150 ml of a 1.7% microfibrillated cellulose was substituted. An envelope of dried Italian salad mix was added and the entire mixture well shaken. A stable dispersion of the spices resulted. The color and texture of the material resembled very closely an authentic Italian dressing.

For comparison purposes, the equivalent amount (2.60 grams) of cellulosic sulfite pulp, cut to pass through a 0.125 inch screen, was added to the same composition in place of microfibrillated cellulose. The cellulosic pulp quickly settled and did not suspend the spices.

EXAMPLE 21

A commercially available dry Thousand Island dressing mix was added to approximately 225 ml of a 2% slurry in water of microfibrillated cellulose and mixed well. A smooth consistency was obtained which appeared quite similar to a regular Thousand Island dressing. The suspension was stable to settling.

The following examples illustrate further uses of microfibrillated cellulose as an aid for emulsifying oils or fats in foods.

EXAMPLE 22

A 2% microfibrillated cellulose slurry was added to a ground pork sausage mixture in an amount equal to 0.2% total cellulose based on final product weight. Upon frying, there was considerably less shrinkage of the sausage link and far less fat rendered as compared to the same ground mixture with no added microfibrillated cellulose.

EXAMPLE 23

A 2.5% microfibrillated cellulose slurry in water was added in the proportion of ⅓ slurry by weight to ⅔ by weight of ground chuck hamburger. This results in a product having 0.83% added cellulose based on final product weight i.e. 27 g of hamburger, 12.67 g added $H_2O$ and 0.33 g of cellulose. On cooking the product remaining weighed 24 g or there was only a 3 gram loss from the original 27 g of hamburger which comes to an 11% weight loss on frying. By comparison a control weighing 40 grams ended up at 26 g after identical frying conditions which corresponds to a 34% weight loss. Not only did the hamburger containing microfibrillated cellulose lose less weight, but it was far juicier and did not have the extremely mealy taste of the control. Thus, addition of the 0.83% cellulose as microfibrillated cellulose served both to reduce cooking losses and to improve overall taste and acceptance of the final product.

EXAMPLE 24

A 2% microfibrillated cellulose slurry in water was added to a commercial meat emulsion used for making hot dogs in an amount equal to 2% cellulose based on total weight of product. After stuffing, smoking and cooking the resultant wieners had a juicier taste and an improved smoke flavor retention as compared with an equivalent wiener without microfibrillated cellulose. Further, there is considerably less formation of fat globules throughout the final product. Palate response was excellent.

EXAMPLE 25

Example 24 was repeated using a commercial bologna emulsion with 3% cellulose based on final product. As compared with the same bologna without microfibrillated cellulose, the resulting bologna has vastly improved response to lowered formation of fat pockets which is one of the major problems in the industry. The product was also juicier and had better flavor retention than the control.

EXAMPLE 26

A low calorie whipped dessert topping was made by mixing together 2.2% cellulosic pulp, 6% sugar, 8% soybean oil and 83.8% water. The mixed ingredients formed a slurry which was passed through an homogenizer having an 8000 psig pressure for ten passes. A whipped topping was produced with a smooth, consistent texture. The topping may, but need not be, further whipped in a blender.

In the cosmetics industry, particularly in the area of skin care, a few basic materials are incorporated into different oil based formulations. The most common of these materials are glycerine and propylene glycol which are used as moisturizing ingredients. When microfibrillated cellulose is produced in glycerol or propylene glycol sufficient body is imparted to the moisturizer so that expensive oils are not required. This not only lowers the costs, but also is an advantage for controlling oily skin. The translucent glycerine-cellulose (MFC) and propylene glycol-cellulose (MFC) give a stable suspension of smooth consistency quite like a commercial hand cream. The high absorbency of the microfibrillated cellulose may additionally be used to carry other agents as a slow release vehicle. The other agents may be bacteriostats or other special skin care agents.

EXAMPLE 27

A 2% slurry of cellulosic pulp in glycerine was passed through a Manton-Gaulin homogenizer for 950 seconds at 8000 psig for 12 passes to a final temperature of 135° C. The result was a stable suspension of smooth consistency quite similar to a commercial hand cream. To this suspension base may be added various aroma contributing ingredients, lanolin, other softening oils, cleansing agents or bacteriocides as desired.

EXAMPLE 28

Example 27 was repeated, using however propylene glycol as the liquid carrier. The resulting product was similar to the glycerine based product.

EXAMPLE 29

A 2% slurry of fluffed sulfite pulp in water containing 0.5% sodium carboxymethyl cellulose was passed through the homogenizer at 8000 psig for 600 seconds or 10 passes to a final temperature of 100° C. A thick opaque paste was obtained which had an excellent consistency for cosmetic cream based uses, showing that water can also be used in addition to glycols. Various aroma contributing ingredients, lanolin, other softening oils, cleansing agents or bacteriocides may be added to this base as in Example 27.

The microfibrillated cellulose useful in the invention is more specifically defined as cellulose having a water retention value over 280%, a settling volume after 60 minutes in a 0.5% by weight suspension in water of greater than 60% and a rate of degradation increase by hydrolysis at 60° C. in one molar hydrochloric acid at least twice as great as cellulose beaten to a Canadian Standard Freeness value of 50 ml. Further and more detailed information concerning microfibrillated cellulose, as well as its preparation, may be found in our aforesaid copending application Ser. No. 107,446, the disclosure of which is hereby incorporated by reference.

We claim:

1. A cosmetic base comprising a suspension of a finely divided cosmetic material in a liquid suspending medium which swells cellulose, said suspension containing microfibrillated cellulose in an amount ranging from 0.25% to an amount such that it is present as the major ingredient of the suspension, said proportions being based on the weight of cellulose solids present as microfibrillated cellulose as compared to the total weight of the suspension, said amount being sufficient to produce a stable, homogeneous suspension, said microfibrillated cellulose having a settling volume after 60 minutes in a 0.5% by weight suspension in water of greater than 60%.

2. The cosmetic base of claim 1 in which the liquid suspending medium is glycerine.

3. The cosmetic base of claim 1 in which the liquid suspending medium is propylene glycol.

4. The cosmetic base of claim 1 in which the liquid suspending medium is water.

* * * * *